(12) United States Patent
Ahn et al.

(10) Patent No.: US 9,155,764 B1
(45) Date of Patent: Oct. 13, 2015

(54) EXPANDED UTILITY OF RED-CELL DERIVED MICROPARTICLES (RMP) FOR TREATMENT OF BLEEDING

(75) Inventors: Yeon S. Ahn, Miami, FL (US); Wenche Jy, Miami, FL (US); Lawrence L. Horstman, Miami, FL (US)

(73) Assignee: University of Miami, Miami, FL (US)

( * ) Notice: Subject to any disclaimer, the term of this patent is extended or adjusted under 35 U.S.C. 154(b) by 155 days.

(21) Appl. No.: 13/357,106

(22) Filed: Jan. 24, 2012

Related U.S. Application Data (63) Continuation-in-part of application No. 11/792,399, filed as application No. PCT/US2005/044064 on Dec. 7, 2005, now Pat. No. 8,105,632.

(60) Provisional application No. 61/457,203, filed on Jan. 28, 2011, provisional application No. 60/633,417, filed on Dec. 7, 2004.

(51) Int. Cl.
    A61K 35/18 (2015.01)
    A01N 1/02 (2006.01)

(52) U.S. Cl.
    CPC .. A61K 35/18 (2013.01); A01N 1/02 (2013.01)

(58) Field of Classification Search
    None
    See application file for complete search history.

(56) References Cited

U.S. PATENT DOCUMENTS

| | | | |
|---|---|---|---|
| 4,529,561 A * | 7/1985 | Hunt et al. | 264/4.3 |
| 5,690,963 A * | 11/1997 | Spargo et al. | 424/533 |
| 7,811,558 B2 | 10/2010 | Ho et al. | |
| 2008/0057505 A1 | 3/2008 | Lin et al. | |
| 2008/0069807 A1 | 3/2008 | Jy et al. | |

FOREIGN PATENT DOCUMENTS

| | | |
|---|---|---|
| JP | 2008-522974 A | 7/2008 |
| WO | WO-00/29029 A1 | 5/2000 |
| WO | WO-2006/062945 A2 | 6/2006 |

OTHER PUBLICATIONS

Yamaguchi et al., J. Biochem., 110:355-359 (1991).*
Schrier et al., Clin. Exp. Immunol, 11:235-244 (1972).*
Ratajczak et al., Leukemia, 20:1487-1495 (2006).*
Lew et al., J. Cell Biol. 106:1893-1901 (1988).*
Hagerstand et al, Biochem. Biophys. Acta., 982:179-186 (1989).*
Butikofer abstract (1987).*
Rubin Thesis (2007).*
Bode et al., Blood, 77:887-895 (1991).*
Salzer et al., Transfusion, 48:451-462 (2008).*
Rybak et al., Biomat. Art. Cells Immob. Biotech., 21(2):101-118 (1993).*
Willekens et al., Brit. J. Haem., 141:549-556 (2008).*
Whitlow et al., Blood, 81:510-516 (1993).*
Diaz, Blood, 87:295-2961 (1996).*
Bevers et al., Blood, 79:380-388 (1992).*
Nomura et al., Atherosclerosis 158:277-287 (2001).*
Harris et al., JBC, 276(25):22722-22731 (2001).*
Lelkes et al., JBC, 260(3):1796-1803 (1985).*
Hamilton et al., J. Lipid Res., 21:981-992 (1980).*
Yamaguchi et al., J. Biochem., 106:1080-1085 (1989).*
Casals et al., Chem. Phys. Lip., 125:139-146 (2003).*
Hannon T, Gjerde KP: The contemporary economics of transfusions. In Perioperative Transfusion Medicine; Speiss RD, Spence RK, Shander A (eds.), Lippincott Williams and Wilkins, p. 13 (2006).
Mannucci PM: Desmopressin (DDAVP) in the treatment of bleeding disorders: the first 20 years. Blood 1997; 90(7): 2515-21.
Hedner U: NovoSeven as a universal hemostatic agent. Blood Coagul Fribrinolysis 2000; 11(Suppl 1): S107-11.
Hawskworth JS, et al: Evaluation of lyophilized platelets as an infusible hemostatic agent in experimental non non-compressible hemorrhage in swine. J Thromb Haemost 2009; 7(10): 1663-71.
Jy W, et al.: Thrombin generation profiles are qualitatively and quantitatively distinct in microparticles derived from red cells (RMP), platelets (PMP), and endothelia (EMP). Blood 2006; 108(11): 499a (Ab1759).
Hemker, H. C.: Calibrated automated thrombin generation measurement in clotting plasma. Pathophysiol Haemost Thromb 33 (1), 4-15 (2003).
Luddington, R., et al.: Clinical measurement of thrombin generation by calibrated automated thrombography requires contact factor inhibition. J Thromb Haemost 2 (11), 1954-1959 (2004).
Bidot, L., et al.: Microparticle-mediated thrombin generation assay: increased activity in patients with recurrent thrombosis. J Thromb Haemost 6, 913-919 (2007).
Davis CL, et al.: Thromboelastography for the prediction of bleeding after transplant renal biopsy. J Am Soc Neph 1995; 6(4): 1250-5.
Ronald A, et al.: Can the use of thromboelastography predict and decrease bleeding and blood and blood product requirements in adult patients undergoing cardiac surgery? Interact CardioVas Thorac Surg 2005;4:456-63.
Plotkin AJ, et al: A reduction in clot formation rate and strength assessed by thromboelastography is indicative of transfusion requirements in patients with penetrating injuries. J Trauma 2008; 64(2 Suppl.): S 64-8.
Ahn YS, et al.: Red cell derived microparticles (RMP) as hemostatic agent to treat bleeding disorders: The mode of action of RMP. JTH (Suppl. 2): 269(2011) (Presented at the International Society of Thrombosis & Hemostasis, Jul. 26, 2011, Kyoto, Japan).

(Continued)

*Primary Examiner* — Blaine Lankford
*Assistant Examiner* — Thomas J Visone
(74) *Attorney, Agent, or Firm* — Venable LLP; Stefan J. Kirchanski (57) ABSTRACT

Red blood cell membrane derived microparticles (RMP) are safe, economical, effective hemostatic agents in the treatment of a wide range of bleeding conditions and can be considered as universal hemostatic agents. RMP are produced from red blood cells using a high-pressure extrusion membrane shear process and can be lyophilized after production and retain activity even when stored at room temperature. RMP can be administered to original donors (autologous treatment), thus avoiding transfusion complications, or can be administered to blood type compatible recipients. RMP produced from type O, Rh negative red cells can be given to any person regardless of blood type. RMP can be administered to reduce excessive bleeding resulting from trauma, surgeries, invasive procedures and various bleeding disorders such as platelet disorders, either congenital or acquired, and coagulation disorders, either congenital or acquired.

11 Claims, 8 Drawing Sheets

(56) References Cited

OTHER PUBLICATIONS

Levi M. et al., "Fibrinogen-Coted Albumin Microcapsules Reduce Bleeding in Severely Thrombocytopenic Rabbits", Nature Medican, Jan. 1999, vol. 5 No. 1, p. 107-111.

McGill M. et al., "Platelet Membrane Vesicles Reduced Microvascular Bleeding times in thrombocytopenic Rabbits", The Journal of Laboratory and Clinical Medicien, Feb. 1987, vol. 109, No. 2, p. 127-133.

Combes V. et al., "In Vitro Generation of Endothelial Microparticles and Possible Prothrombotic Activity in Patients With Lups Anticoagulant" The Journal of Clinical Investigation , Jul. 1999, vol. 104, No. 1, p. 93-102.

Biro E. et al., "Human Cell-Derived Microparticles Promote Thrombus Formation In Vivo in a Tissue Factor-Dependent Manner." Journal of Thrombosis and Haemostasis:, Dec. 2003, vol. 1, No. 12, p. 2561-2568.

AHN, "Cell-Derived Microparticles: 'Miniature Envoys With Many Faces'" *Journal of Thrombosis and Haemostasis*, 3: 884-887, 2005.

George, et al., "Isolation of Human Platelet Membrane Microparticles From Plasma and Serum", *Blood*, 60. 4, 1982.

Jimenez et al., "Endothelial Cells Release Phenotypically and Quantitatively Distinct Microparticles in Activation and Apoptosis", *Thrombosis Research*, 109, 175-180, 2003.

Wenche et al., "Clinical Significance of Platelet Microparticles in Autoimmune Thrombocytopenias", *The Journal of Laboratory and Clinical Medicine*, 119, No. 4, 334-345, 1992.

Wolf, "The Nature and Significance of Platelet Products in Human Plasma", *Brit. J. Haernat*, 13, 269-288, 1967.

Jimenez et al., Activation-Derived Endothelial Microparticles (EMP) Are Elevated in Thrombotic Thrombocytopenia Pupura (TTP): Detection of von Willebrand Factor (vWF)—Positive EMP during the acute phase of TTP in vitro and in vivo. Blood, vol. 100, No. 11 Abstract No. 40 44th Annual Meeting of the American Society of Hematology, Blood 2002, vol. 100.

Warkenton, T.E., An Overview of the Heparin-Induced Thrombocytopenia Syndrome. Seminars in Thrombosis and Homeostasis, vol. 30, No. 3, 2004.

Mallat et al., Elevated levels of Shed Membrane Microparticle with Procoagulant potential in the peripheral circulating blood of patients with acute coronary syndromes, Circulation 20000, vol. 101, p. 841-843.

Piacibello et al., 2000. Ex vivo expansion of megakaryocytes. Transfusion Science, vol. 22: 107-110.

Solheim and Wesenberg, 2001. Rational use of blood products. European Journal of Cancer, vol. 37:2421-2427.

Ahn et al., U.S. Appl. No. 13/982,224, filed Jul. 26, 2013, "Expanded Utility of Red Cell-Derived Microparticles (RMP) for Treatment of Bleeding".

International Search Report and Written Opinion in PCT International Application No. PCT/US2012/023020, dated Aug. 14, 2012.

Ahn, Red cell microparticles (RMP) as hemostatic agent: summary of recent advance', American Society of Hematology, 53rd ASH Annual Meeting and Exposition, San Diego, Dec. 11, 2011, No. 2260.

Office Action in Japanese Patent Application No. 2013-551393, dated Sep. 30, 2014.

Blajchman MA, "Novel platelet products, substitutes and alternatives," Transfus Clin Biol 8, (2001), 267-71.

Galan AM et al., "Possible hemostatic effect of synthetic liposomes in experimental studies under flow conditions," Hematologic, 2002, 87:615-23.

Jy W et al, "Microparticles in stored red blood cells as potential mediators of transfusion complications," Transfusio, 2011, 51(4):886-93.

Jy W et al., "Red cell derived microparticles as hemostatic agent," Thromb & Haemost, 2013, 110:751-60.

Lacroix R et al. "Revisited role of microparticles in arterial and venous thrombosis," J Throm Haemost, 2013, 11(Suppl.1): 24-35.

Okamura, Y et al. "Hemostatic effects of phospholipid vesicles carrying fibrinogen gamma-chain dodecapeptide in vitro and in vivo," Bioconjugate Chem 16, 2005, 1589-1596.

Parnham MJ, Wetzig H, Toxicity screening of liposomes, Chem Phys Lipids 1993;64:263-74.# 2595.

Taylor FB et al., "Infusion of phospholipid vesicles amplifies the local thrombosis to TNF and anti-protein C into a consumptive response," Thromb Haemost, 1996, 75:574-84.

\* cited by examiner

EXPANDED UTILITY OF RED-CELL DERIVED MICROPARTICLES (RMP) FOR TREATMENT OF BLEEDING

CROSS-REFERENCE TO PRIOR APPLICATIONS

The present application is a non-provisional of and claims benefit and priority from U.S. Provisional Application No. 61/457,203, filed on Jan. 28, 2011 and is also a continuation-in-part of and claims benefit and priority from U.S. patent application Ser. No. 11/792,399, filed 6 Jun. 2007, now U.S. Pat. No. 8,105,632, issue date of 31 Jan. 2012, which application was the U.S. National Phase of PCT/US2005/044064, filed 7 Dec. 2005, which was based on U.S. Provisional Patent Application No. 60/633,417, filed 7 Dec. 2004; all of the aforementioned applications are incorporated herein by reference.

U.S. GOVERNMENT SUPPORT

N/A

BACKGROUND OF THE INVENTION

1. Area of the Art

The present invention is in the area of hematology and more specifically in the area of novel treatment for bleeding.

2. Description of the Background

The invention relates to improved compositions comprising red cell membrane-derived microparticles (RMP) that enhance blood coagulation, platelet activity, and promote blood clot formation and to a method for treating excessive bleeding including but not limited to those due to disorders of platelets and blood coagulation and to methods for manufacturing such compositions. The inventive compositions are useful in minimizing blood loss in a mammal, in particular in patients undergoing surgical or medical invasive procedures and those with trauma where blood loss can be substantial. RMP correct hemostatic abnormalities arising from blood clotting factor deficiencies, as well as from deficiency in platelet numbers (thrombocytopenia) and/or function (platelet dysfunction).

Excessive bleeding is among the most common of life-threatening complications in trauma and bleeding complications in both clinics and hospitals. The bleeding patient poses a major medical challenge in all medical specialties such as surgery, trauma, obstetrics/gynecology, cardiology, neurology, hematology, etc. At present, transfusion of banked blood products is the mainstay of treatment for excessive bleeding, but transfusion is very expensive [1] and carries risks of serious short- and long-term complications.

Timing is critical in bleeding patients. Prompt intervention is essential to patient management, but often many hours are required to type, cross-match, and deliver blood from the blood bank to the patient. Therefore, blood transfusion as presently employed often fails to save the lives of many bleeding victims. Furthermore, since blood products must often be given before the cause of bleeding is identified, transfusion may fail to arrest bleeding and merely replaces lost blood while the bleeding continues. Days or weeks of investigation may be required to find the underlying cause of excessive bleeding.

Treatments for bleeding differ depending on etiology of the bleeding. For example, (1) when excessive bleeding develops due to low platelet counts (thrombocytopenia) platelet transfusion or other measures to raise platelet counts must be used to arrest bleeding. In the case of impaired platelet function (dysfunction) treatment to improve platelet function or platelet transfusion are employed. (2) In the case of coagulation disorders, in which one or more of 13 clotting factors are low in level or are defective or inhibited, missing clotting factors must be supplied to arrest bleeding. In hemophilia A, factor VIII must be administered whereas in hemophilia B factor IX must be administered. Without these specific therapies to correct underlying etiology, bleeding will not stop and patients will be exposed to endless transfusions.

To save the lives of bleeding victims, we need agents that can be administered safely and immediately, at reasonable cost. An ideal product could be administered to patients on a moment's notice, regardless of the underlying etiology of the bleeding. No such agent is yet available in spite of a century-long search.

New and better products are urgently needed to promptly arrest bleeding in all situations regardless of the cause of bleeding. Such products will save many lives and will avoid needless transfusions and associated complications. Our RMP product meets all requirements of safety and efficacy required of a cost effective universal hemostatic agent. RMP can be infused at a moment's notice and is effective in the treatment of most bleeding conditions. It is also expected to be less costly and safer compared to other products intended for this purpose.

As already explained, blood can be a life-saving resource, but blood is becoming increasingly scarce and expensive due to rising demand, limited supply, and more stringent regulations. According to the National Blood Data Resource Center, 4.5 million people receive transfusion annually. The cost for red cell transfusions alone is $24 billion per year. This does not include platelets and other blood products. The hospital cost for transfusion-related adverse effects exceeds $10 billion per year [1]. Transfusions are associated with many short- and long-term complications including anaphylaxis, hemolytic reactions, transfusion induced immune suppression, graft-versus host disease, transfusion related acute lung injury (TRALI) and transmission of pathogens such as hepatitis, HIV and prion diseases (mad cow disease).

This situation can only get worse with increasing age of the population. For example, to prevent heart attacks, strokes and other thromboses that affect the elderly, increasing numbers of the patients are being treated with anticoagulants or anti-platelet therapy. The former includes Coumadin, Heparin, LMWH (low molecular weight Heparin), fondaparinux (Arixtra) and a new generation of oral thrombin or FXa inhibitors such a as dabigatran (Pradaxa) and rivaroxaban (Xarelto). The later include aspirin, Plavix (clopidogrel) and other antiplatelet drugs. All these new anticoagulants and antiplatelet medications have serious side effects of promoting bleeding and, thus, increase bleeding complication and, hence, the demand for more transfusions.

Some of the older drugs such as Coumadin and Heparin have antidotes. Therefore, bleeding from overdose of Coumadin can be treated with vitamin K, and Heparin can be neutralized by an antidote, such as protamine, to thereby limit bleeding. However, there is no effective antidote for new anticoagulants such as low molecular weight heparin, e.g., Lovenox (enoxaparin) (which can be partially reversed by protamine) and Fragmin (dalteparin), Arixtra (fondaparinux), Pradaxa (dabigatran) and Xarelto (rivaroxaban) and for most antiplatelet drugs (e.g., aspirin, Plavix and their analogs). Therefore, bleeding resulting from new anticoagulants and antiplatelet drugs imposes new challenges in patient management. At present, this bleeding is treated blindly with transfusion of blood/blood products. RMP administration can correct or improve coagulation abnormalities induced by both the new and older types of "blood thinners" as well as antiplatelet drugs as is shown in FIGS. 4A, 4B, 4C, 4D, 4E and 4H.

Although transfusion of banked blood is a mainstay of therapy for bleeding, other measures have been advocated, such as antifibrinolytic agents, DDAVP [2], but these treatments are not widely used because their efficacy is unproven. Recombinant Factor VIIa (i.e., NovoSeven) gained much attention and showed great promise [3], but its use is limited by prohibitive cost (e.g., in excess of $1 million for a single patient with high levels of FVIII inhibitors) and by reports of serious thrombotic complications. RMP has great potential for wide application in in various bleeding disorders and corrects hemostatic abnormalities induced by most anticoagulants including new generation anticoagulants as well as by most antiplatelet drugs. It can be stored in ambulances for use in emergency medicine (e.g., at accident sites) and in operating rooms, clinics, dental offices, pharmacies and hospitals, since it is stable at room temperature, is reasonable in cost and shows no sign of adverse effects.

Platelet MP (PMP) and lyophilized whole platelets (LyoPLT) [4] have also been proposed for treatment of bleeding. Lyophilized platelets (LyoPLT) are under current study but may be impractical compared to RMP due to (i) the high costs of scarce platelets, (ii) risk of thrombogenesis, and (iii) immuno-reactivity. The total volume of circulating platelets in blood is only 20 ml, about 1/250 that of red cells, so starting material is costly and scarce. Platelets are highly immunogenic due to HLA, ABO, Rh, and platelet-specific antigens, which are impractical to cross match, hence adverse reactions are frequent. Furthermore, platelets are known to carry tissue factor (TF) which is thrombogenic. In contrast, RMP have none of these disadvantages.

SUMMARY OF THE INVENTION

The present invention (RMP) shows significant advantages over existing treatment options. In contrast to blood bank products, (a) RMP have indefinite shelf-life with room temperature storage and does not need to be stored in blood banks; (b) RMP produced from type O Rh negative red cells (universal RMP) can be administered immediately without cross-matching; and (c) RMP can often substitute for bloodbank products. In addition, use of autologous RMP (made from patient's own blood), can be used to eliminate major risks of transfusion complications.

RMP have many advantages as hemostatic agents, inter alia:

(1) Ease and Economy of Production.

Red cells (RBC) are by far the most abundant blood cells, assuring an essentially unlimited and economical source for RMP production. A single conventional blood donation (500 mL) is sufficient to produce RMP to treat at least two patients. Out-dated RBC in the blood bank, which is otherwise discarded, can be used as a source of RMP production.

(2) Minimal Immune Reactions.

RBCs are the least immunogenic and safe to transfuse to type compatible recipients. RMP produced from universal donors (type O, Rh negative) can be stored and safely infused into patients of any blood type. This is not the case of other blood cells such as platelets.

(3) Autologous Option.

RMP can be made from the patient's own blood and infused back to the original donors when they bleed or are at high risk of bleeding. The use of autologous RMP will eliminate complications of allogeneic blood transfusion. This option is well suited to patients who anticipate bleeding problems such as prior to surgery or diagnostic or therapeutic invasive procedures or chemotherapy which often induces bone marrow failure and severe thrombocytopenia. Systemic diseases may also result in thrombocytopenia. Those who take anticoagulants or antiplatelet drugs or agents frequently suffer bleeding complications. They can prepare their own autologous RMP to be used safely in case of bleeding. In addition, religious groups which refused normal transfusion could benefit by this option.

(4) Universal RMP.

In emergency situations there is no time to type and cross match. RMP produced from type O and Rh negative red cells can be infused promptly to any recipient, regardless of blood type.

For reason of safety, donors for "universal RMP" should be screened carefully to ensure that they are negative for hepatitis, HIV, CMV or other transmittable infections. Healthy universal donors can donate blood as often as monthly. Accordingly ample resources are available for universal RMP.

RMP produced by the methods described herein can be used fresh or stored. Fresh RMP can be made in local blood banks or laboratories and distributed to operating rooms, clinics, hospitals and other medical settings. RMP can be stocked almost anywhere including in pharmacies, ambulances, operating rooms, clinics and hospitals. Initial work on RMP produced the product by various types of red cell membrane disruption such as sonication and treatment with ionophores. However, these methods were cumbersome, difficult to scale up and might produce RMP that were suboptimal. We have now developed a method of producing RMP using high-pressure membrane shear technology. This method produces RMP free of any additives and is readily scalable and easy to implement.

Using our improved methodology a supplier of RMP (such as a pharmaceutical company) can produce a large quantity of universal RMP or blood type specific RMP, lyophilize them and market them as hemostatic agents.

Emergency rooms, trauma centers can treat accident victims (e.g. from vehicular accidents). In the military, RMP can be used for first-responder management of battlefield wounds. RMP can be used to treat and manage sport induced trauma or injury, and for injuries in natural disasters such as earthquakes or hurricanes etc.

The use of RMP will reduce the strain on limited supplies at blood banks. In addition, since RMP produced from expired blood have been found to be as effective as RMP from very fresh blood, their production will not place added burden on supplies. It is anticipated that RMP will replace the need for transfusion in many situations. Since RMP have unlimited shelf-life, and can be produced economically, their use is expected to be at least cost-competitive with currently used blood products, resulting in an overall substantial saving in health care costs.

DESCRIPTION OF THE FIGURES

FIG. 4A: Thrombocytopenia from aplastic anemia (platelet count 1,000/µL); FIG. 4B: Thrombocytopenia from ITP (platelet count 70,000/µL); FIG. 4C: Platelet dysfunction caused by aspirin; FIG. 4D: Platelet dysfunction caused by Plavix; FIG. 4E: Coagulopathy caused by Coumadin; FIG. 4F: Coagulopathy caused by Lovenox; FIG. 4G: Coagulopathy caused by Pradaxa; FIG. 4H: Congenital hemophilia A with a mild inhibitor;

DETAILED DESCRIPTION OF THE INVENTION

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide methods for the production, storage and use of RMP.

Disclosed herein are unique hemostatic benefits of high-pressure shear produced RMP as effective and safe treatments for a wide variety of bleeding situations. Accordingly, in addition to treatment of bleeding resulting from thrombocytopenia, platelet dysfunction and surgical procedures and trauma, compositions and methods are provided for treating coagulopathy induced by anticoagulant drugs or systemic disease or clotting factor deficiency. These and other disorders that result in bleeding are treated by the administration of an effective amount of high-pressure shear RMP to a patient in need of treatment.

Effective dosages of RMP can be determined without undue experimentation by those of skill in the art and are generally expected to be between $10^6$ and $10^{12}$ particles/kg of body weight, more usually between $10^8$ and $10^{10}$ particles/kg. RMP may be administered in any suitable pharmaceutical composition according to the pharmaceutical arts, including normal saline or other physiologically acceptable buffers known to those of skill in the art, and optionally with additional therapeutic compounds, excipients and carriers as may be considered advantageous. The pH of the suspending buffer should generally be equal to or below 7.4.

RMP may be administered by any convenient and effective means known to those of skill in the art, particularly intravenously, or by direct application (e.g. topically, or by local injection) to a site where hemostasis is needed or desired. Such means will be known and/or easily determined without undue experimentation.

Further details about pharmaceutical compositions and administration of RMP can be found in the parent application (U.S. patent application Ser. No. 11/792,399) of the current application.

Figure 3A:
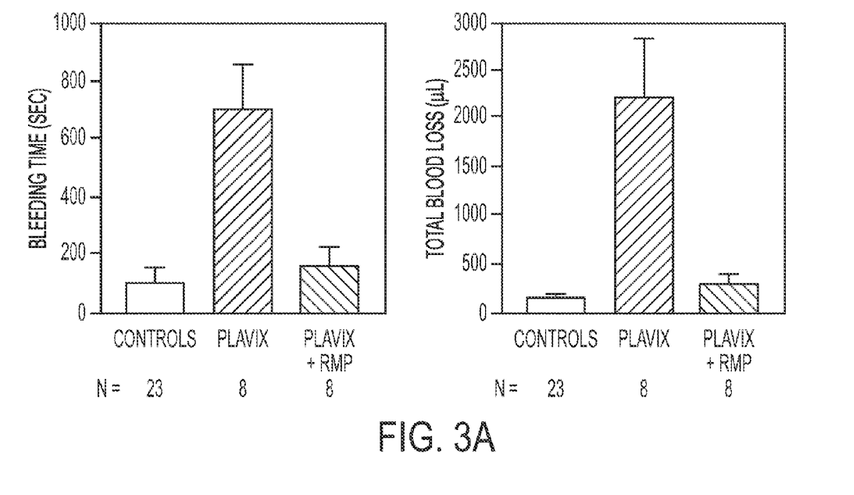
FIG. 3A is a bar graph demonstrating hemostatic effect of RMP produced using a high pressure extrusion device French Press (note that RMP shortened rat tail bleeding time and blood loss in rats with platelet dysfunction induced by the anti-platelet drug Plavix.
Figure 3B:
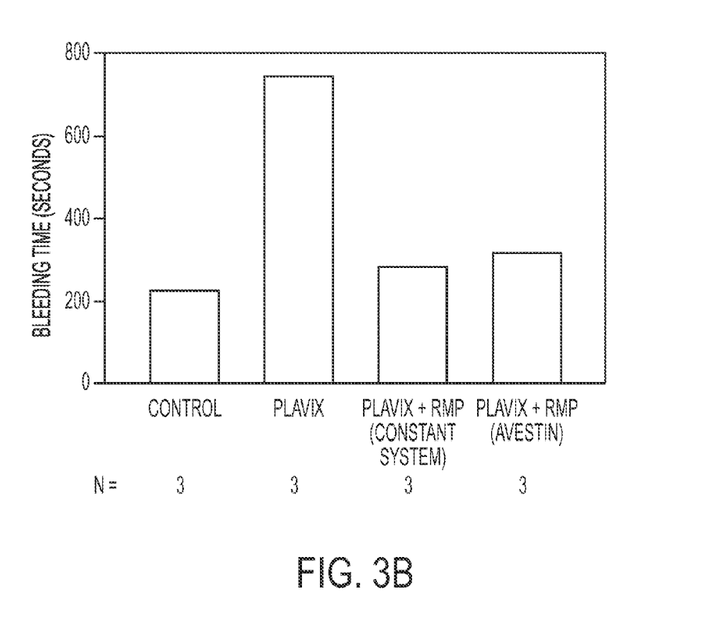
FIG. 3B is a bar graph demonstrating hemostatic effect of RMP produced using high-pressure extrusion devices from Avestin or Constant Systems (note that RMP produced by these two devices shortened rat bleeding time in a manner similar to those produced by French Press)

An improved method of RMP production is provided herein; this improved method employs shear induced by high pressure extrusion to enable economically feasible, large-scale RMP production without the use of additives and includes a method of long-term RMP storage. For RMP production by high shear principle, we used a French Press, but we also tested RMP produced by other instruments employing the same principle, such as those from Avestin and Constant Systems in vitro. These high pressure extrusion induced shear devices all generate RMP with similar procoagulant properties in vivo as shown in FIG. 3B. Table 1 compares the flow cytometric markers measured on RMP produced by the French Press with RMP produced by either a Constant System device or by an Avestin device. These results demonstrate that RMPs generated by different devices using similar high pressure extrusion are similar.

TABLE 1

| Production | RMP markers (Counts/ uL) | | |
|---|---|---|---|
| Device | Annexin V | Glycophorin A | Ulex europaeus |
| French Press | 8,426 | 27,145 | 42,016 |
| Constant Systems | 7,547 | 22,271 | 33,286 |
| Avestin | 4,274 | 10,005 | 18,512 |

Example 1

Production of RMP (Laboratory Scale)

For a single batch, 30 mL packed cells from blood bank are diluted with 60 mL of isotonic saline containing 1.5 mM EDTA pH 7.4. Cells are washed 3 times with the same EDTA/saline by centrifuging 15 min. each at 750×g at room temp. The final resuspension is brought to volume 60 mL, which is then drawn into the stainless-steel pressure cell of the French Press (Thermo-Electron Inc.) and then expelled at an internal pressure of 25,000 psi at rate 1.5 mL/min (achieved by adjustment of the needle valve). The resulting effluent was centrifuged at low speed (750×g) to remove the small number of unbroken cells, and the supernatant was then centrifuged at 18,000×g for 45 min. to sediment the RMP. One of ordinary skill in the art will appreciate that filtration and other separation techniques can be employed to remove the unbroken cells. The RMP were then washed at the same speed in isotonic saline (no EDTA) and refrigerated overnight prior to lyophilization. This procedure is >99% efficient in the sense that the starting red cells are almost entirely converted to uniform RMP of suitable size range.

Example 2

Potential for Scale-Up

This principle (shear induced by high-pressure extrusion) can be readily adapted to commercial-scale production. It was arrived at only after extensive experimentation with many other methods such as ionophore, sonic disruption, osmotic rupture, and others. The basic function of a French Press is to apply shear to fluid suspended cells. The cell suspension is placed in a pressure cell where pressure is applied by means of a hydraulic ram whereupon the pressurized suspension is forced (extruded) through the orifice of a needle valve into a region of atmospheric pressure. The great drop in pressure as the cells pass through the orifice applies great shear force to the biomembranes. The process is controlled by setting a target pressure on the hydraulic ram and controlling the needle valve to achieve a given flow rate. A drawback to the French Press is that the volume processed is limited by the size of the pressure cell (typically 100 mL) and the need to manipulate the needle valve accurately. Extensive study of French Press-treated membranes has demonstrated that the system generally produces inside out membrane vesicle. A number of related high-pressure shear systems obviate some of the disadvantages of the French Press. Pumped fluid homogenizers pressurize a larger volume of fluid and force it through a spring loaded valve into a region of atmospheric pressure. The effect is the same as the French Press except that the valve spring can be more reproducibly preset. Other pumped fluid homogenizers dispense with any type of valve and simply extrude the cell suspension (at a selected pressure) through a narrow channel or a fixed orifice into a region of atmospheric pressure. Both the pressure setting and the orifice diameter or channel diameter/length can be selected to achieve the desired results. Pumping in such systems can be achieved by reciprocating piston systems so that the device is essentially a self-filling French Press. Alternatively, the effluent stream from the high pressure extrusion system can be directed to impinge on a surface (e.g., a metal plate) to enhance the disruption of RBC. One of ordinary skill in the art can readily adjust the target pressure and the valve/channel openings of such devices to achieve production of high quality RMP.

Example 3

Lyophilization for Storage

An RMP batch (from Example 1) made the previous day was mixed with optimal amounts of albumin, glucose, sorbitol and/or trehalose, then pipetted in 1.0 mL aliquots into 2 mL lyophilizing vials, then placed in the tray of a Triad Freeze Dry System (Labconco, Inc.). The instrument operation is divided into programmable segments. Our experiments established the following optimal program settings. Samples are first subjected to a 4-hour "Pre-freeze" phase, with brief vacuum, during which temperature drops to −75° C. Segment 1. After switching to full vacuum (<0.07 mbars), temperature is ramped up (at 0.27° C./min) to −30° C. and held for 2-hr. Segment 2. Temperature is slowly increased (at 0.04° C./min) to −25° C., and held for 2-hr. Segment 3. Temperature is ramped to −15° C. at 0.04° C./min, and held for 12-hr. Final Step. Vials are sealed in vacuum; rubber stoppers were pre-placed on the vials and pressed on to seal by pressure plate. After removing vials, aluminum tab seals are crimped on; vials are stored at room temp. Activity recovered is equal or superior to freezing at −70° C. for at least 90 days, with no decline observed. Of course, the material can be stored at low temperature to ensure long-term activity, but our tests indicate that even a protracted period of storage at room temperature does not destroy activity.

The inventors found that RMP lyophilized in this manner show excellent efficacy in vitro and in animal models, as compared with fresh RMP (prior to freezing or lyophilizing). Persons of ordinary skill in the art will appreciate that some variation in the procedural parameters will produce an equally superior product and that further improvement in properties of the RMP product may be made by routine adjustments of the procedural parameters. As mentioned above, the lyophilized RMP show no decline of activity for at least 90 days at room temperature.

Example 4

Figure 1:
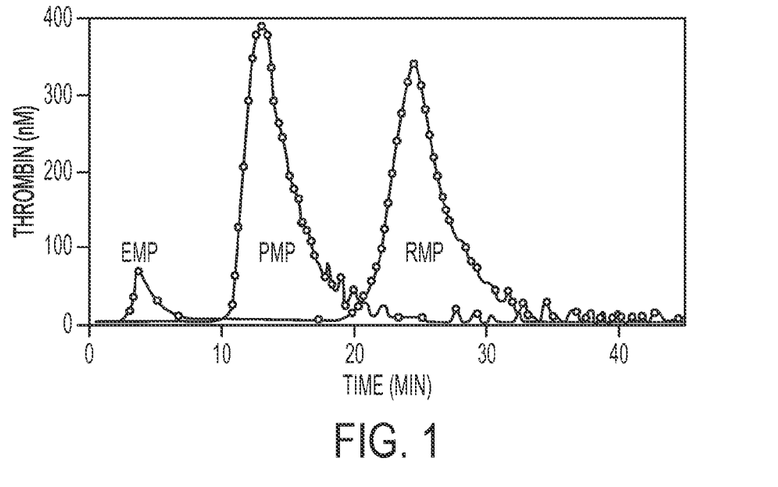
FIG. 1 is a graph showing thrombin generation by RMP as wells as by microparticles from other cells (note that the pattern of thrombin generation differs among RMP, PMP (platelet MP), EMP (endothelial MP) in terms of incubation time and amplitude of thrombin generation)

Thrombin Generation Assay (TGA) (FIG. 1)

This assay was based on the method and software of Hemker et al. [6], termed "Calibrated Automated Thrombin" (CAT) generation assay [7], adapted by the inventors to measure activity of microparticles [8]. The method measures a change in signal when a fluorescent substrate for thrombin is cleaved. Procedure: In the experiment shown, RMP were generated by exposure of washed fresh RBC from normal donor to calcium ionophore A23187 (10 µM) for 1 hr. In a later study (not shown), we generated RMP by means of the high pressure shear extrusion method described above and confirmed that RMP produced using both methods show similar hemostatic activity. PMP (platelet microparticles) were generated by exposure of human platelet rich plasma to ADP (10 µM) for 30 min. EMP (endothelial microparticles) were obtained from the supernatant of cultured human renal microvascular endothelial cells activated by tumor necrosis factor (TNF-α) (10 nM) for 24 hrs. In all cases unbroken cells were removed by centrifugation (700×g for 15 min), and the resulting microparticles were sedimented (15,000×g for 30 min) and pellets were washed twice, then resuspended to equal microparticle concentrations ($1 \times 10^8$ counts/mL, final concentration) based on counts by flow cytometry. Then 10 µL of microparticles were mixed with 90 µL of corn trypsin inhibitor (25 µg/mL)-treated particle free plasma (PFP) after which the CAT test was initiated by addition of calcium. Relevant data are chiefly the lag time, seen on the x-axis, and peak thrombin generated, seen on the y-axis in units/nM. The inventors' laboratory was first to document thrombin generation by RMP [5]. The time-course of thrombin generation by RMP is distinctive, as shown. Note the long lag-time of RMP compared to PMP and EMP, which is attributed to the absence of tissue factor (TF). This is a great advantage of RMP as hemostatic agent. RMP, however, generate equally strong amplitude once coagulation is initiated. As seen in FIG. 1, the mode of thrombin generation differed among EMP, PMP and RMP. Accordingly, combined use of EMP and PMP along with RMP could be of benefit in certain clinical settings. MP types with distinct hemostatic property can be combined to exert optimal hemostatic efficacy in reducing bleeding. This is an important rational for supporting MP combination therapy.

Example 5

Figure 2:
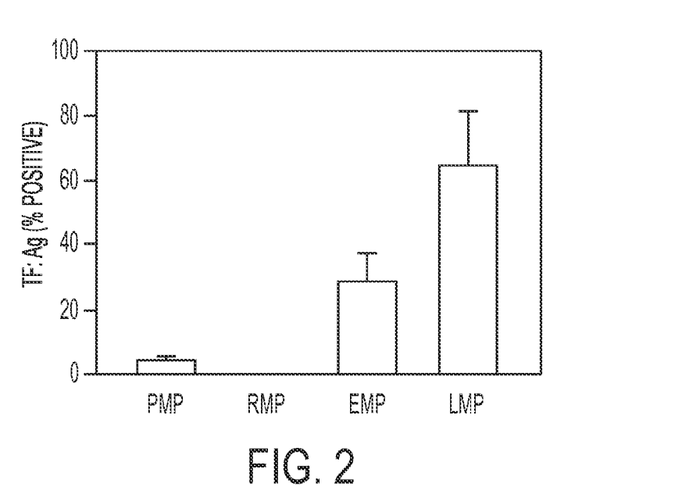
FIG. 2 is a bar graph demonstrating the relative absence of Tissue Factor (TF) expression on RMP as compared to microparticles derived from other cell types.

Absence of TF Expression on RMP (FIG. 2)

The method used was flow cytometric detection of TF antigen using PE/Cy5-labeled anti-TF (American Diagnostica). PMP, EMP and RMP were prepared as described in the previous section. LMP (leukocyte microparticles) were prepared by incubating neutrophils ($5 \times 10^6$/mL) with lipopolysaccharide (LPS, 10 ng/mL final concentration). The neutrophils were isolated by standard procedures (Ficol-Hypaque density centrifugation). All microparticles were adjusted to equal concentration ($1 \times 10^8$/mL). TF was measured in flow cytometry by double-staining (anti-TF and FITC-Ulex lectin) prior to aspiration into the flow cytometer.

Event detection was triggered by the green fluorescent signal. Results are given as percentage of microparticle-positive events that were also positive for TF. It is apparent that TF expression on microparticles would promote systemic thrombosis. However, TF can benefit local hemostasis at the site of injury. Accordingly proper combination of RMP and tissue factor expressing microparticles will have therapeutic advantage of certain bleeding condition as described above.

The figure demonstrates that TF is not detected on RMP but is easily detected on other cell-derived microparticles: those from platelet (PMP), endothelia (EMP) and leukocytes (LMP). This result is consistent with literature identifying TF on all microparticles except t RMP. TF is the main physiological initiator of coagulation and thrombosis. So that the absence of TF on RMP indicates a high degree of safety, i.e., inability to generate thrombin, except a local site of injury where TF is present. In other words, RMP are not efficient in initiating thrombin generation, but contribute robustly to its generation upon exposure of TF, such as at a bleeding site, thus providing effective hemostasis locally but not systemically.

Figure 5:
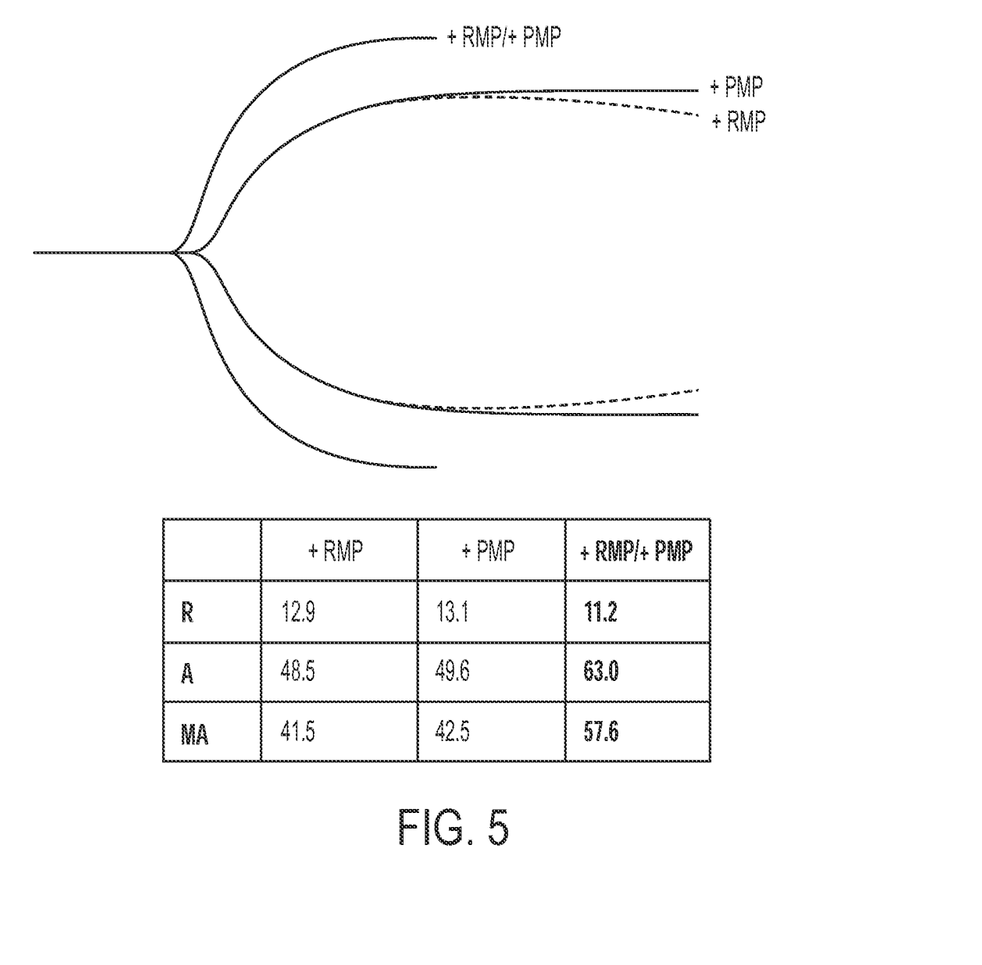
FIG. 5 shows a TEG tracing with RMP and PMP alone and combination of RMP and PMP demonstrating shortening of R time, increasing A and enhancing MA indicative of a synergistic effect from the combination.

Because RMP, PMP, EMP, LMP have different hemostatic property as demonstrated in FIGS. 1 and 2, use of RMP combined with other MP such as PMP can exhibit a synergistic effect. FIG. 5 demonstrates that combination of RMP with PMP exhibit synergistic effect in hemostasis when examined by TEG. Use of the combination shortened clotting time (R) and increased speed of clot formation (A) and enhanced clot strength (MA) compared to RMP or PMP alone.

Example 6

Use of RMP to Treat Platelet Dysfunction (FIG. 3)

In the parent of the instant application, applicants presented data showing that infusion of RMP shortened tail bleeding time in thrombocytopenic rats.

The question addressed by this study was whether RMP were able to reduce bleeding from platelet dysfunction as well. We induced platelet dysfunction in rats by intravenous injection of Plavix (10 mg/kg). FIG. 3 shows that platelet dysfunction induced by Plavix increased bleeding time and blood loss by at least 5-fold compared to controls, and some animals did not stop bleeding at all and expired. However, all eight animals treated with RMP (dose of $2.0 \times 10^9$/kg) showed almost complete normalization of bleeding time and blood loss.

The experiments were conducted in Sprague-Dawley rats. The procedure was begun by weighing the animal (range 250-350 g) and anesthetizing them by adding 1-2 mL of Isoflurane to a sealed container in which the rat was placed. Once sedated, the rat was placed on a special platform that allows a technician to intubate it. The animal constantly received oxygen and Isoflurane from a respirator to maintain anesthesia. The animal was then affixed to a surgical board and a rectal thermometer is used to monitor body temperature. A heating pad was placed under the board to maintain body temperature. When stable, the neck of the animal was shaved and a small incision was made to find the jugular vein and the carotid artery. Any slight bleeding during this procedure was stopped with a cautery tool. Both the jugular vein and the carotid artery were cleaned and isolated from surrounding connective tissue. Before inserting the cannulas, blood flow was controlled by tying a section of the vein and artery. Once the cannulas were in place, they were secured with sutures and the incision closed. The jugular vein was later used to inject test substances (RMP, medications) and the carotid artery was used to supply vital fluids (lactated Ringer's) and to monitor heart rate and blood pressure. This allows the rat to survive for the required 3-4 hours. Bleeding was initiated by cutting a 2 mm segment of a toe and all blood was collected in tube for "total blood loss" and time to cease bleeding was measured.

Baseline data was obtained for n=23 untreated animals (controls; at left). Platelet dysfunction was induced by infusion of clopidogrel (Plavix) at a dose of 10 mg/kg through the catheter 10 min. prior to bleeding. The center bar shows increased bleeding time and blood loss due to clopidogrel. The error bar is +/−SEM. The left panel is a comparison of bleeding time between controls, animals treated with Plavix, and animals treated with both Plavix and RMP. The right panel is a comparison of total blood loss between the same groups. RMP administered at a dose of $2.0 \times 10^8$/kg in volume 400 μL five minutes prior to bleeding gave correction of bleeding time and blood loss to near-normal range, as shown (right bars). Note the near normalization of bleeding time and blood loss by RMP infusion.

In our animal model, improved instrumentation was used to measure heart rate, blood pressure, respiration and temperature. Vital signs were closely monitored before and after RMP infusion. Bleeding time and total blood loss were measured after cutting toe, as described. All treated animals were observed for up to four hours post-treatment (under anesthetic). None of the RMP-treated animals showed indication of thrombosis or signs of adverse change in temperature, heart rate, respiration, or neurological signs. This included two cases tested at double the full effective dose; no further reduction in bleeding time (below normal) was observed. This indicates absence of prothrombotic effects, and suggests complete safety in all cases studied thus far. Since RMP do not carry tissue factor (TF), there is no theoretical reason to expect adverse effects. The apparent absence of adverse effects even at high dose is considered to be an important advantage of RMP compared to other products intended for this purpose.

We also studied the effectiveness of RMP generated by different high pressure instruments (e.g., Avestin, Constant system) using the rat model described above. These RMP were as effective in shortening tail bleeding time as were RMP produced by the French Press high pressure instrument (as shown in FIG. 3A). Table 1 compares the flow cytometric markers measured on RMP produced by the French Press with RMP produced by either a Constant Systems device or by an Avestin device. These results demonstrate that RMP produced using various high pressure extrusion devices are similar.

Example 7

Clinical Study of RMP on Various Bleeding Disorders by Means of TEG

Bleeding time (BT) was formerly used to predict risk of bleeding at surgery but is now replaced by thromboelastograph (TEG) measurements because of superior reproducibility and the additional important data provided by TEG instruments [9-11]. TEG is the best in vitro assay to predict risk of bleeding in vivo and its value in assessing hemostasis is well accepted. TEG measurement is increasingly utilized to assess bleeding with invasive procedures or surgery such as renal biopsy [8], cardiovascular surgery [9, 10] and trauma [11]. It is such a widely accepted practice now for surgeons to preorder blood for transfusion based on TEG abnormality in an effort to prevent excessive bleeding.

TEG Protocol:

Blood samples were drawn in citrated vacutainers from patients with various bleeding disorders. Blood samples were pipetted (330 µL) into the cup of the "TEG Haemoscope" (Haemonetics Co.), then 10 µL of saline (control, without RMP). RMP produced through high-pressure extrusion was added to each well at the dose of $6.8 \times 10^7$ particles to bring the final RMP concentration to $2 \times 10^8$/mL. The reaction was initiated by adding 10 µL of $CaCl_2$. TEG tracings were obtained without and with RMP, and alteration of TEG parameters by addition of RMP was evaluated. The quantity of RMP added was calculated from the therapeutic dose determined in animal experiments.

Figure 4:
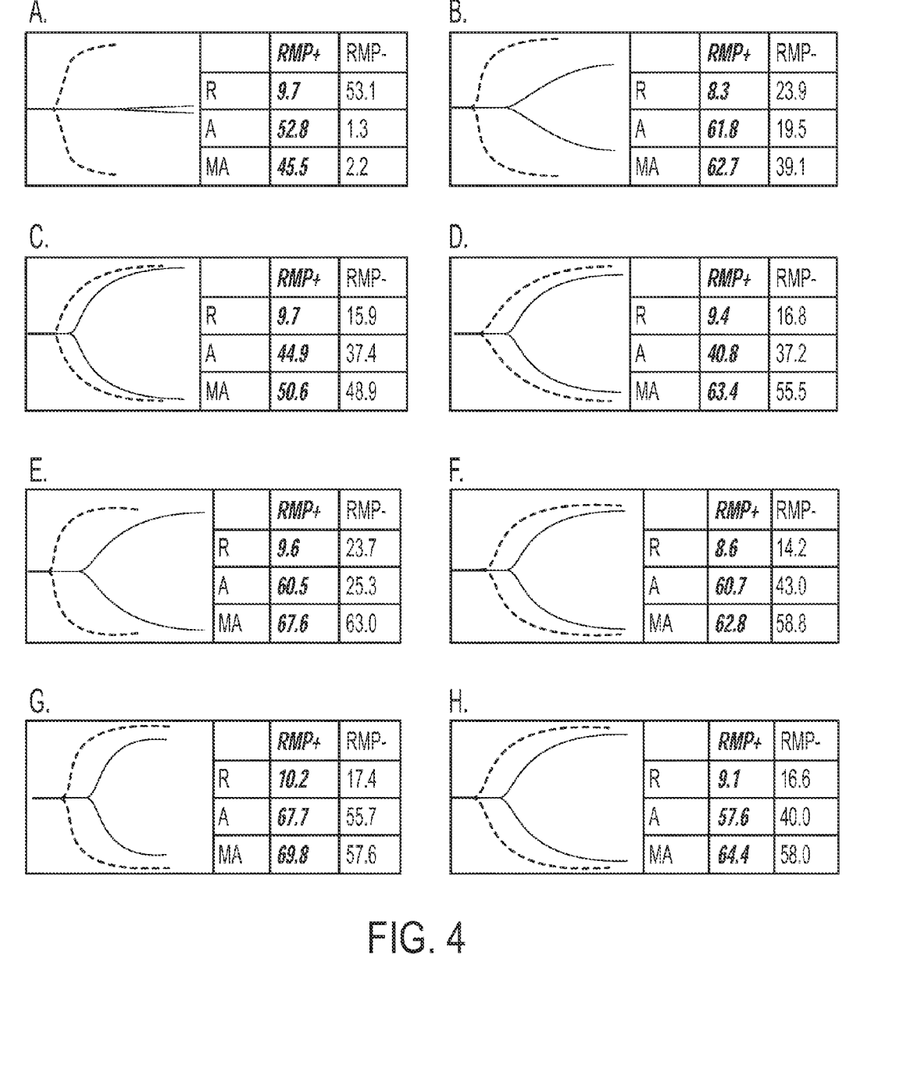
FIG. 4 shows TEG profiles of bleeding disorders in the presence or absence of RMP.

FIGS. 4 A-G are examples of clinical studies to evaluate hemostatic property of RMP. It should be noted that TEG tracings without RMP are shown in unbolded solid lines and tracing after addition of RMP are shown in bolded broken lines. In each figure, changes in R, A and MA are compared in the boxes next to figures. These findings indicate potential value of RMP to treat various bleeding disorders. The applicants found that TEG gave results which corresponded closely to in vivo (animal) studies, in particular, results with Plavix, building confidence that TEG is a good surrogate for in vivo studies. This confirms literature that TEG correlates closely with bleeding time in vivo (human). TEG is also more reproducible, faster, and supplies additional important measurement parameters [9-11].

Parameters Measured.

TEG measures the delay of initiation of clotting (R), the rate of clot formation (a, angular rise rate), and maximum amplitude (MA). A high risk of bleeding is detected as a high R with a low a, or low MA measure value.

In aplastic anemia (FIG. 4A), bone marrow fails to produce sufficient red cells, white cells and platelets; this patient had fewer than 1% of normal platelets (1,000/µL vs. normal value of 250,000/µL). The figure shows almost no clotting in absence of RMP, but with a therapeutic dose of RMP a nearly normal trace is seen as indicated by fast initiation (R=9.7 min, from 53.5), a rate of rise (a=52.8, from 1.3) and an increase of MA (from 2.2 to 45.5) as detailed in the figures' side boxes.

In ITP (Idiopathic Thrombocytopenic Purpura) (FIG. 4B), platelets are destroyed by an autoimmune reaction; this patient had only 28% of the normal number of platelets. In absence of RMP, clotting is delayed nearly three-fold longer than normal (R=23.9) and rate is weak as seen in the low slope (a=19.5). A normal profile is restored by therapeutic dose of RMP (R=8.3, a=61.8).

In this patient (FIG. 4C), platelet dysfunction was due to aspirin, which inhibits platelet function and can result in serious bleeding, especially in combination with other disorders or medications. Note the elimination of the prolonged lag time (R) by RMP.

In this case (FIG. 4D) platelet dysfunction was due to therapy with Plavix (clopidogrel), which inhibits platelet function as does aspirin but by a different mechanism (blockade of ADP receptors). Despite a different mechanism of platelet dysfunction, RMP corrected the prolonged lag time.

Coumadin (a.k.a. Warfarin) is most widely used "blood thinners" prescribed for prevention and treatment of thrombosis. It acts by preventing effective production of the several clotting factors that require vitamin K. Overdose of Coumadin, which happens commonly, can lead to serious bleeding. In this patient (FIG. 4E), notice that RMP fully corrected the prolonged lag time (R) and slow rate (a). Platelet counts were normal in this patient.

Many new anticoagulants will soon come to market. The old as well as the new anticoagulants belong to one of four groups: 1) Vitamin K antagonists such as Coumadin; 2) Heparin and low molecular weight heparin; 3) inhibitors of thrombin (anti-factor IIa) such as dabigatran; and 4) inhibitors of prothrombinase complex (anti-factor Xa) such as fondaparinux and rivaroxaban. The new anticoagulants are increasingly employed. Low molecular Heparin (LMWH) and especially enoxaparin (Lovenox) and dalteparin (Fragmin) are now widely used. These new anticoagulants do not have antidotes, therefore hemorrhagic complications from new anticoagulants is very problematic. FIG. 4F shows that RMP correct coagulation abnormality induced by Lovenox. Similar correction by RMP was seen in other LMWH such as dalteparin (Fragmin) and fondaparinux (Arixtra) as well as dabigatran (Pradaxa), a new oral thrombin inhibitor (FIG. 4 G) which is more convenient and practical to use than existing anticoagulants. RMP corrects clotting abnormalities induced by anticoagulants from any of the four groups. Therefore, RMP should be effective against bleeding resulting from any new drugs belonging to one of these groups.

Hemophilia A is an inherited disorder marked by ready bleeding due to low levels of functional factor VIII (FVIII). Painful and debilitating bleeding in the joints and mucous membranes are common, and brain hemorrhage can be fatal. Treatment is infusion of FVIII concentrates but this treatment is often ineffective due to formation of inhibitors of the FVIII administered. This patient (FIG. 4H) had congenital Hemophilia A and developed mild inhibitor. The figure shows that RMP corrected prolonged lag (R) and normalized rate (a) of clotting.

Examples 8

Mode of Action of RMP in Hemostasis

Figure 6:
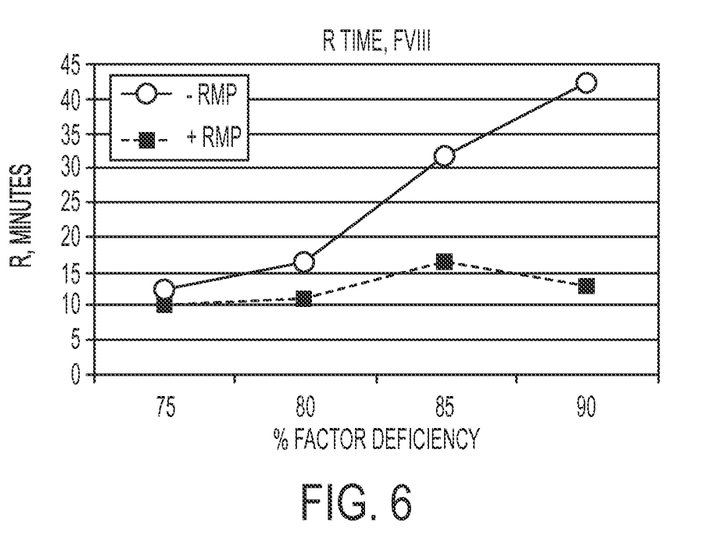
FIG. 6 is a graph showing that RMP increases procoagulance of factor VIII deficient plasma, corroborating the results shown in Table 2.

To investigate how RMP exert diverse actions in hemostasis, we mixed RMP with factor deficient plasma and studied alteration of procoagulance with TEG. Addition of RMP to factor deficient plasma shortened clotting time (R), increased rated of clotting (a) and enhanced clot strength (MA). However degree of increasing procoagulance by RMP differed between clotting factor deficiency. Effects of RMP in Factor II, V, VII, VIII, IX, X, XI XII, XIII deficiency are shown in the Table 2 [12]. The increase in procoagulance by RMP was most pronounced in Factor VIII (see FIG. 6) and Factor IX deficient plasmas where RMP could correct deficiencies as low as 5-10% of the normal levels of the clotting factors. In all cases addition of RMP resulted in a significant correction of clotting time.

Other Bleeding Conditions Seen Corrected.

RMP was observed to correct the abnormality in the following cases judged by TEG: (i) Patients with mild inhibitors to Factor IX, XI; (ii) patients treated with heparin, low molecular weight heparin (Lovenox, Fragmin) and Arixtra; (iii) patients with DIC; (iv) chronic liver disease; (v) thrombocytopenia from bone marrow failure such as aplastic anemia, myelodysplastic syndrome, leukemias (data not shown).

Figure 7A:
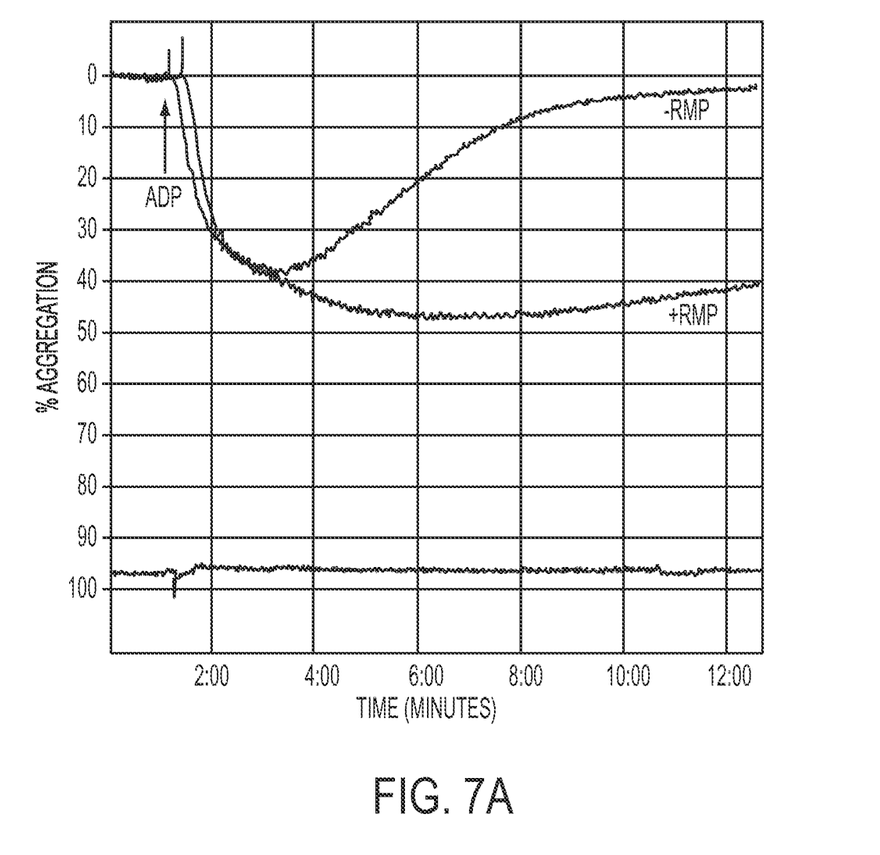
FIG. 7A is a graph showing that RMP enhance platelet aggregation at a low dose (0.2 µM) of ADP.
Figure 7B:
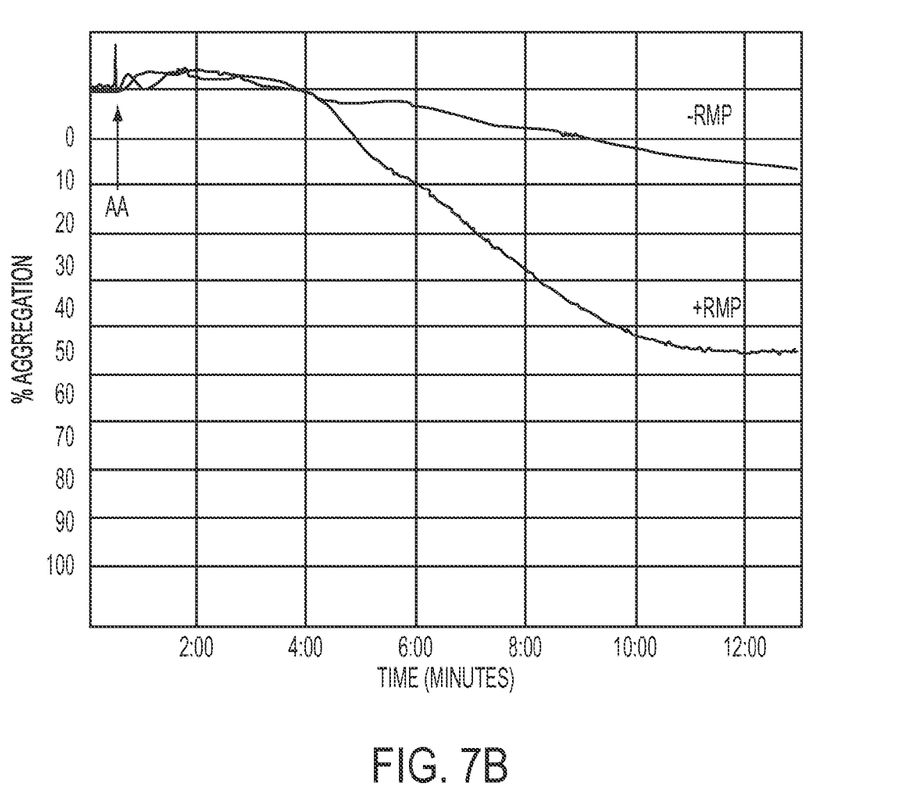
FIG. 7B is a graph showing that RMP enhance platelet aggregation at a low dose (0.3 mM) of arachidonic acid.
Figure 8:
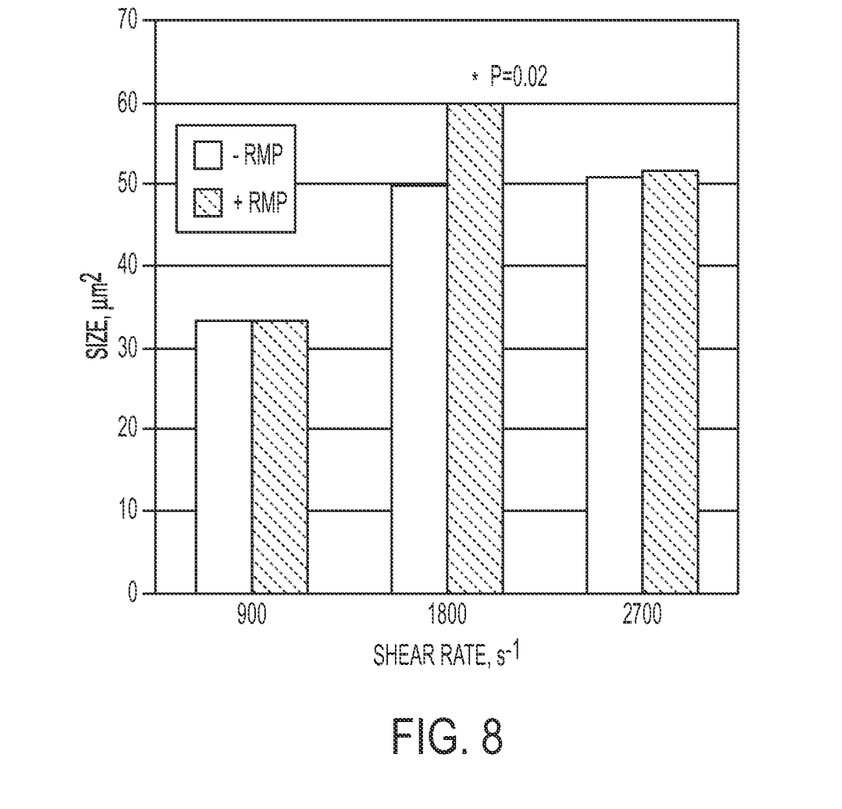
FIG. 8 is a bar graph showing RMP enhanced platelet adhesion.

FIGS. 7A and 7B show the effect of RMP on platelet aggregation and adhesion. At low concentrations of ADP (FIG. 7A) and arachidonic acid (FIG. 7B), RMP enhanced platelet aggregation measured by Chrono-Log aggregometry. We also studied the effect of RMP on platelet adhesion by a cone-well device (Diamed IMPACT-R), where RMP enhanced platelet adhesion by increasing the sizes of aggregates. FIG. 8 shows the enhancement in platelet adhesion. Note the statistically significant (*P=0.02) increase in size of aggregates of platelets by RMP at shear rate $(S^{-1})=1800$, that resemble venous blood flow in vivo [12].

TABLE 2

RMP enhance procoagulance in factor deficient plasmas.

|  |  | R (min) | A (degree) | MA (mm) |
|---|---|---|---|---|
| F II | RMP− | 8.7 | 63.6 | 33 |
|  | RMP+ | 8.4 | 68.1 | 37 |
|  | Δ | −0.3 | 4.5 | 4 |
| F V | RMP− | 11.2 | 62.1 | 29.2 |
|  | RMP+ | 11.1 | 64.8 | 28.7 |
|  | Δ | −0.1 | 2.7 | −0.5 |
| F VII | RMP− | 11.6 | 57.7 | 29.6 |
|  | RMP+ | 11.3 | 62 | 25.5 |
|  | Δ | −0.3 | 4.3 | −4.1 |
| F VIII | RMP− | 30.8 | 23.1 | 26.3 |
|  | RMP+ | 16.6 | 52.6 | 29.7 |
|  | Δ | −14.2 | 29.5 | 3.4 |
| F IX | RMP− | 77.2 | 1.1 | 7.2 |
|  | RMP+ | 28.2 | 12.6 | 27.8 |
|  | Δ | −49 | 11.5 | 20.6 |
| F X | RMP− | 11.2 | 62.1 | 29.1 |
|  | RMP+ | 11.1 | 64.8 | 28.7 |
|  | Δ | −0.1 | 2.7 | −0.4 |
| F XI | RMP− | 14.8 | 55.6 | 27.6 |
|  | RMP+ | 12.2 | 50.2 | 47.7 |
|  | Δ | −2.6 | −5.4 | 20.1 |
| F XII | RMP− | 13.1 | 32.9 | 25.4 |
|  | RMP+ | 11.1 | 55.3 | 35.2 |
|  | Δ | −2 | 22.4 | 9.8 |
| F XIII | RMP− | 8.5 | 56.2 | 20.8 |
|  | RMP+ | 8.2 | 57.7 | 24.1 |
|  | Δ | −0.3 | 1.5 | 3.3 |

The following claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

REFERENCES

References and publications cited herein are hereby incorporated by reference
1. Hannon T, Gjerde K P: The contemporary economics of transfusions. In Perioperative Transfusion Medicine; Speiss R D, Spence R K, Shander A (eds.), Lippincott Williams and Wilkins, p. 13 (2006).
2. Mannucci P M: Desmopressin (DDAVP) in the treatment of bleeding disorders: the first 20 years. *Blood* 1997; 90(7): 2515-21.
3. Hedner U: NovoSeven as a universal hemostatic agent. *Blood Coagul Fribrinolysis* 2000; 11(Suppl 1): S107-11.
4. Hawksworth J S, et al: Evaluation of lyophilized platelets as an infusible hemostatic agent in experimental non non-compressible hemorrhage in swine. *J Thromb Haemost* 2009; 7(10): 1663-71.
5. Jy W, Bidot L, Jimenez J J, Horstman L L, Bang J, Lin A, ZambranoJr W, Ahn E, Ahn Y-S: Thrombin generation profiles are qualitatively and quantitatively distinct in microparticles derived from red cells (RMP), platelets (PMP), and endothelia (EMP). *Blood* 2006; 108(11): 499a (Ab1759).
6. Hemker, H. C.: Calibrated automated thrombin generation measurement in clotting plasma. *Pathophysiol Haemost Thromb* 33 (1), 4-15 (2003).
7. Luddington, R. and Baglin, T.: Clinical measurement of thrombin generation by calibrated automated thrombography requires contact factor inhibition. *J Thromb Haemost* 2 (11), 1954-1959 (2004).
8. Bidot, L., Jy, W., Bidot Jr, C., Jimenez, J. J., Fontana, V., Horstman, L. L and Ahn, Y. S.: Microparticle-mediated thrombin generation assay: increased activity in patients with recurrent thrombosis. *J Thromb Haemost* 6, 913-919 (2007).
9. Davis C L, Chancier W L: Thromboelastography for the prediction of bleeding after transplant renal biopsy. *J Am Soc Neph* 1995; 6(4): 1250-5.
10. Ronald A, Dunning J: Can the use of thromboelastography predict and decrease bleeding and blood and blood product requirements in adult patients undergoing cardiac surgery? *Interact CardioVas Thorac Surg* 2005; 4:456-63.
11. Plotkin A J, Wade C E, Jinkins D H, et al: A reduction in clot formation rate and strength assessed by thromboelastography is indicative of transfusion requirements in patients with penetrating injuries. *J Trauma* 2008; 64(2 Suppl.): S 64-8.
12. Ahn Y S, Jy W, Johansen M, Horstman L L: Red cell derived microparticles (RMP) as hemostatic agent to treat bleeding disorders: The mode of action of RMP. JTH (Suppl. 2): 269(2011) (Presented at the International Society of Thrombosis & Hemostasis, Jul. 26, 2011, Kyoto, Japan).

What is claimed is:

1. A process for producing red cell membrane derived microparticles (RMP) having hemostatic activity without thrombogenic activity comprising the steps of:
   suspending red blood cells in an aqueous diluent to form a cell suspension;
   pressurizing the cell suspension;
   extruding the pressurized cell suspension into a region of lower pressure to generate shear forces on the suspended red blood cells whereby the suspended cells are converted into a crude RMP suspension; and
   removing any whole red blood cells from the crude RMP suspension to make a final RMP suspension having hemostatic activity without thrombogenic activity.

2. The process according to claim 1, wherein a French Press is used to pressurize and extrude the cell suspension.

3. The process according to claim 1, wherein whole red blood cells are removed from the crude RMP suspension by centrifugation.

4. The process according to claim 3, wherein RMP are removed from the crude RMP suspension by centrifugation.

5. The process according to claim 1, wherein whole red blood cells are removed from the crude RMP suspension by filtration.

6. The process according to claim 1 further comprising a step of washing the red blood cells with saline prior to the step of suspending.

7. The process according to claim 6, wherein the saline further comprises EDTA.

8. The process according to claim 1 further comprising a step of lyophilizing the final RMP suspension.

9. The process according to claim 1 wherein the red blood cells are from an autologous donor.

10. The process according to claim 1, wherein the red blood cells are selected from the group consisting of type A—Rh positive, type A—Rh negative, type B—Rh positive, type B—Rh negative, type AB—Rh positive, type AB—Rh negative, type O—Rh positive and type O, Rh negative.

11. The process according to claim 10, wherein the red blood cells are type O—Rh negative.

* * * * *